(12) United States Patent
Zhang et al.

(10) Patent No.: US 8,296,247 B2
(45) Date of Patent: Oct. 23, 2012

(54) COMBINATION MACHINE LEARNING ALGORITHMS FOR COMPUTER-AIDED DETECTION, REVIEW AND DIAGNOSIS

(75) Inventors: Heidi Daoxian Zhang, Los Gatos, CA (US); Patrick Bernard Heffernan, Los Gatos, CA (US)

(73) Assignee: Three Palm Software, Los Gatos, CA (US)

( * ) Notice: Subject to any disclaimer, the term of this patent is extended or adjusted under 35 U.S.C. 154(b) by 863 days.

(21) Appl. No.: 12/053,600

(22) Filed: Mar. 22, 2008

(65) Prior Publication Data

US 2009/0171871 A1    Jul. 2, 2009

Related U.S. Application Data

(60) Provisional application No. 60/919,459, filed on Mar. 23, 2007.

(51) Int. Cl.
| | |
|---|---|
| *G06F 15/18* | (2006.01) |
| *G06F 15/00* | (2006.01) |
| *G06E 1/00* | (2006.01) |
| *G06E 3/00* | (2006.01) |
| *G06N 99/00* | (2010.01) |
| *G06N 5/00* | (2006.01) |
| *G06G 7/00* | (2006.01) |

(52) U.S. Cl. ............... 706/12; 706/10; 706/45; 706/924
(58) Field of Classification Search .................... 706/10, 706/12, 20, 48, 924
See application file for complete search history.

(56) References Cited

U.S. PATENT DOCUMENTS

| 5,769,074 A | 6/1998 | Barnhill et al. | |
|---|---|---|---|
| 6,996,549 B2 | 2/2006 | Zhang et al. | |
| 7,298,877 B1 * | 11/2007 | Collins et al. | 382/128 |
| 2004/0264628 A1 * | 12/2004 | Besson | 378/5 |
| 2006/0018548 A1 * | 1/2006 | Chen et al. | 382/190 |
| 2008/0044068 A1 * | 2/2008 | Evertsz et al. | 715/700 |

OTHER PUBLICATIONS

Tsirogiannis,G.L. et al. "Classification of medical data with a robust multi-level combination scheme," Neural Networks, 2004. Proceedings. 2004 IEEE International Joint Conference on, vol. 3, No., pp. 2483-2487 vol. 3, Jul. 25-29, 2004. doi: 10.1109/IJCNN.2004.1381020.*

(Continued)

*Primary Examiner* — Jeffrey A Gaffin
*Assistant Examiner* — Benjamin Buss
(74) *Attorney, Agent, or Firm* — Haynes and Boone, LLP

(57) ABSTRACT

A method of reviewing medical images and clinical data to generate a diagnosis or treatment decision is provided. The method includes receiving, at a computer-aided detection (CAD) system, the medical images and clinical data, processing the medical images and clinical data; to generate initial finding candidates and clustering the initial finding candidates into a plurality of groups. The method further includes classifying the initial finding candidates using machine learning algorithms integrated into the CAD system into one or more categories one or more categories of the initial finding candidates using type 2 fuzz logic, and determining detection and assessment statistics based on at least the assessed categories and classified findings using Bayesian probability analysis. The method also includes modifying the classified findings and assessed categories based on additional interactive input, and generating the diagnosis or treatment decision based on the determined detection, assessment statistics, and the additional interactive input.

8 Claims, 9 Drawing Sheets

OTHER PUBLICATIONS

Glotsos,D. et al. "Automated Diagnosis of Brain Tumours Astrocytomas Using Probabilistic Neural Network Clustering and Support Vector Machines" International Journal of Neural Systems, vol. 15, Nos. 1 & 2 (2005) pp. 1-11.*

John,R.I. et al. "Modeling uncertainty in clinical diagnosis using fuzzy logic," Systems, Man, and Cybernetics, Part B: Cybernetics, IEEE Transactions on, vol. 35, No. 6, pp. 1340-1350, Dec. 2005. doi: 10.1109/TSMCB.2005.855588.*

André, T.C.S.S. et al. "Classification of breast masses in mammograms using neural networks with shape, edge sharpness, and texture features", J. Electron. Imaging 15, 013019 (Mar. 3, 2006); doi:10.1117/1.2178271.*

Penedo,M.G. et al. "Computer-aided diagnosis: a neural-network-based approach to lung nodule detection," Medical Imaging, IEEE Transactions on , vol. 17, No. 6, pp. 872-880, Dec. 1998. doi: 10.1109/42.746620.*

Karnik,N. N. et al. "Type-2 fuzzy logic systems: type-reduction," Systems, Man, and Cybernetics, 1998. 1998 IEEE International Conference on , vol. 2, No., pp. 2046-2051 vol. 2, Oct. 11-14, 1998. doi: 10.1109/ICSMC.1998.728199.*

Chiavaccini,E. et al. "MAP symbol estimation on frequency-flat Rayleigh fading channels via a Bayesian EM algorithm," Communications, 2001. ICC 2001. IEEE International Conference on , vol. 4, No., pp. 1057-1061 vol. 4, 2001. doi: 10.1109/ICC.2001.936804.*

Giger,M.L. et al. "Computer-aided diagnosis of breast lesions in medical images," Computing in Science & Engineering , vol. 2, No. 5, pp. 39-45, Sep./Oct. 2000. doi: 10.1109/5992.877391.*

Hadjiiski,L. et al. "Advances in CAD for diagnosis of breast cancer", Curr Opin Obstet Gynecol. Feb. 2006; 18(1): 64-70. doi: 10.1097/01.gco.0000192965.29449.da.*

Hassanien,A, "Fuzzy rough sets hybrid scheme for breast cancer detection", Image and Vision Computing, vol. 25, Issue 2, Soft Computing in Image Analysis, Feb. 2007, Available Online Jun. 30, 2006. pp. 172-183, ISSN 0262-8856, DOI: 10.1016/j.imavis.2006.01. 026.*

Sampat,M.P. et al. "Computer-Aided Detection and Diagnosis in Mammography" 2005.*

Li,P. et al. "Detecting abnormal regions in colonoscopic images by patch-based classifier ensemble," Pattern Recognition, 2004. ICPR 2004. Proceedings of the 17th International Conference on , vol. 3, No., pp. 774-777 vol. 3, Aug. 23-26, 2004. doi: 10.1109/ICPR.2004. 1334643.*

Wu,Y. et al. "Breast Cancer Diagnosis Using Neural-Based Linear Fusion Strategies", Neural Information Processing, Lecture Notes in Computer Science, 2006, vol. 4234/2006, 165-175, DOI: 10.1007/11893295_19.*

Bazzani,A. et al. "Automatic detection of clustered microcalcifications in digital mammograms using an SVM classifier", ESANN'2000 Proceedings—European Symposium on Artificial Neural Networks, Apr. 26-28, 2000. ISPN 2-930307-00-5, pp. 195-200.*

Noble,J.A. et al. "Ultrasound image segmentation: a survey," Medical Imaging, IEEE Transactions on , vol. 25, No. 8, pp. 987-1010, Aug. 2006. doi: 10.1109/TMI.2006.877092.*

Cheng,H.D. et al. "Computer-aided detection and classification of microcalcifcations in mammograms: a survey", Pattern Recognition, vol. 36, Issue 12, Dec. 2003, pp. 2967-2991.*

Abd-Elfattah et al., "Efficiency of Bayes Estimator for Rayleigh Distribution", *Interstat*, 2006.

André et al., "Classification of Breast Masses in Mammograms Using Neural Networks with Shape, Edge Sharpness, and Texture Features", *Journal of Electronic Imaging*, vol. 15(1), Jan.-Mar. 2006.

Chiavaccini et al., "MAP Symbol Estimation on Frequency-Flat Rayleigh Fading Channels Via a Bayesian EM Algorithm", *IEEE Transactions on Communications*, pp. 1057-1061, 2001.

Demonstration of Matlab Fuzzy Logic Packages, TAMUCC Al Workshop, Jan. 12-13, 2007. Posted Mar. 15-16, 2007, at http://aiworkshop.tamucc.edu/index_files/.

Giger, Maryellen L., "Computer-Aided Diagnosis of Breast Lesions in Medical Images", *Computing in Science and Engineering*, pp. 39-45, Sep./Oct. 2000.

Glotsos et al., "Automated Diagnosis of Brain Tumours Astrocytomas Using Probabilistic Neural Network Clustering and Support Vector Machines", *International Journal of Neural Systems*, vol. 15, Nos. 1 & 2, pp. 1-11, 2005.

Innocent et al., "Computer Aided Fuzzy Medical Diagnosis" *Information Science*, vol. 162, pp. 81-104, 2004.

Innocent et al., "Modeling Uncertainty in Clinical Diagnosis Using Fuzzy Logic", *IEEE Transactions on Systems, Man, and Cybernetics—Part B: Cybernetics*, vol. 35, No. 6, Dec. 2005.

Karnik at at, "Type-2 Fuzzy Logic Systems: Type-Reduction", *IEEE International Conference on Systems, Man, and Cybernetics*, vol. 2, pp. 2046-2051, Oct. 11-14, 1998.

Kundu et al., "Generalized Rayleigh Distribution: Different Methods of Estimations", *Computational Statistics & Data Analysis*, 2005.

Penedo et al., "Computer-Aided Diagnosis: A Neural-Network-Based Approach to Lung Nodule Detection", *IEEE Transactions on Medical Imaging*, vol. 17, No. 6, Dec. 1998.

Tsirogiannis et al., "Classification of Medical Data with a Robust Multi-Level Combination Scheme", *IEEE International Joint Conference on Neural Networks*, vol. 3, pp. 2483-2487, Jul. 25-29, 2004.

Zadeh, L.A., "Fuzzy Logic, Neural Networks, and Soft Computing", *Communications of the ACM*, vol. 37, No. 3, pp. 77-84, Mar. 1994.

Zadeh, L.A., "Fuzzy Sets", *Information Control*, vol. 8, pp. 338-353, 1965.

Zadeh, L.A., "The Concept of a Linguistic Variable and its Application to Approximate Reasoning", *Information Science*, vol. 8, pp. 199-249, 1975.

* cited by examiner

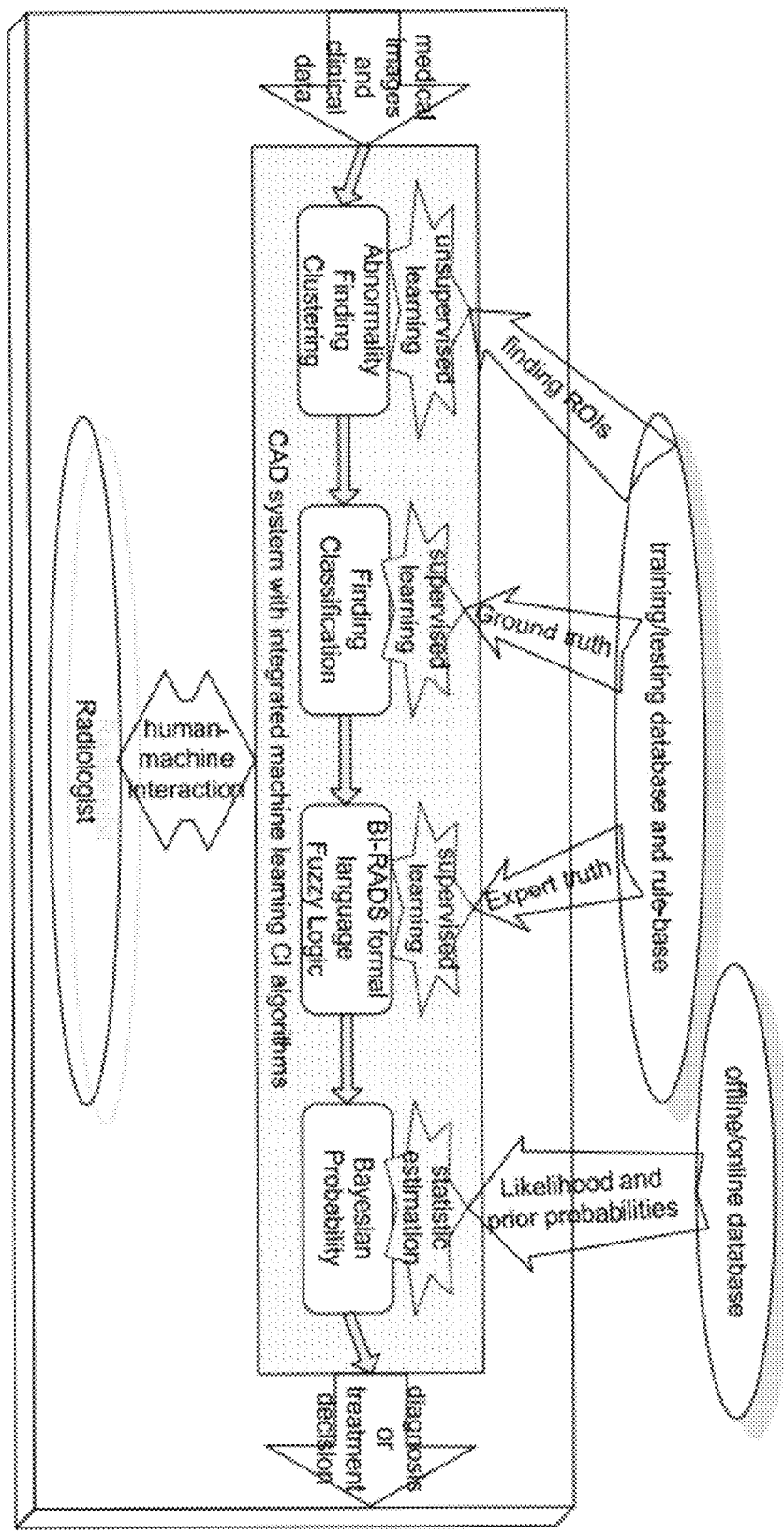
Figure-1: high-level framework

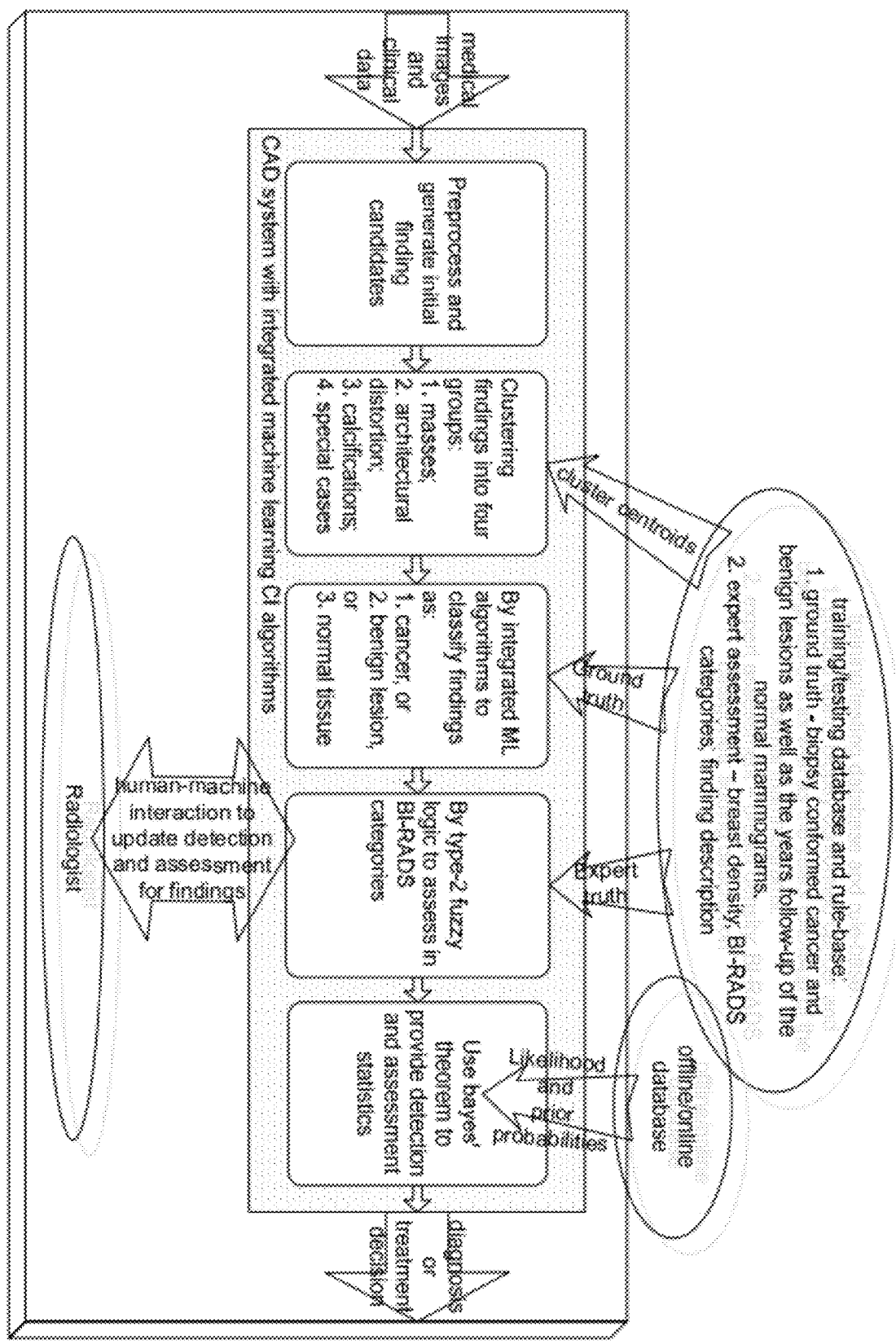

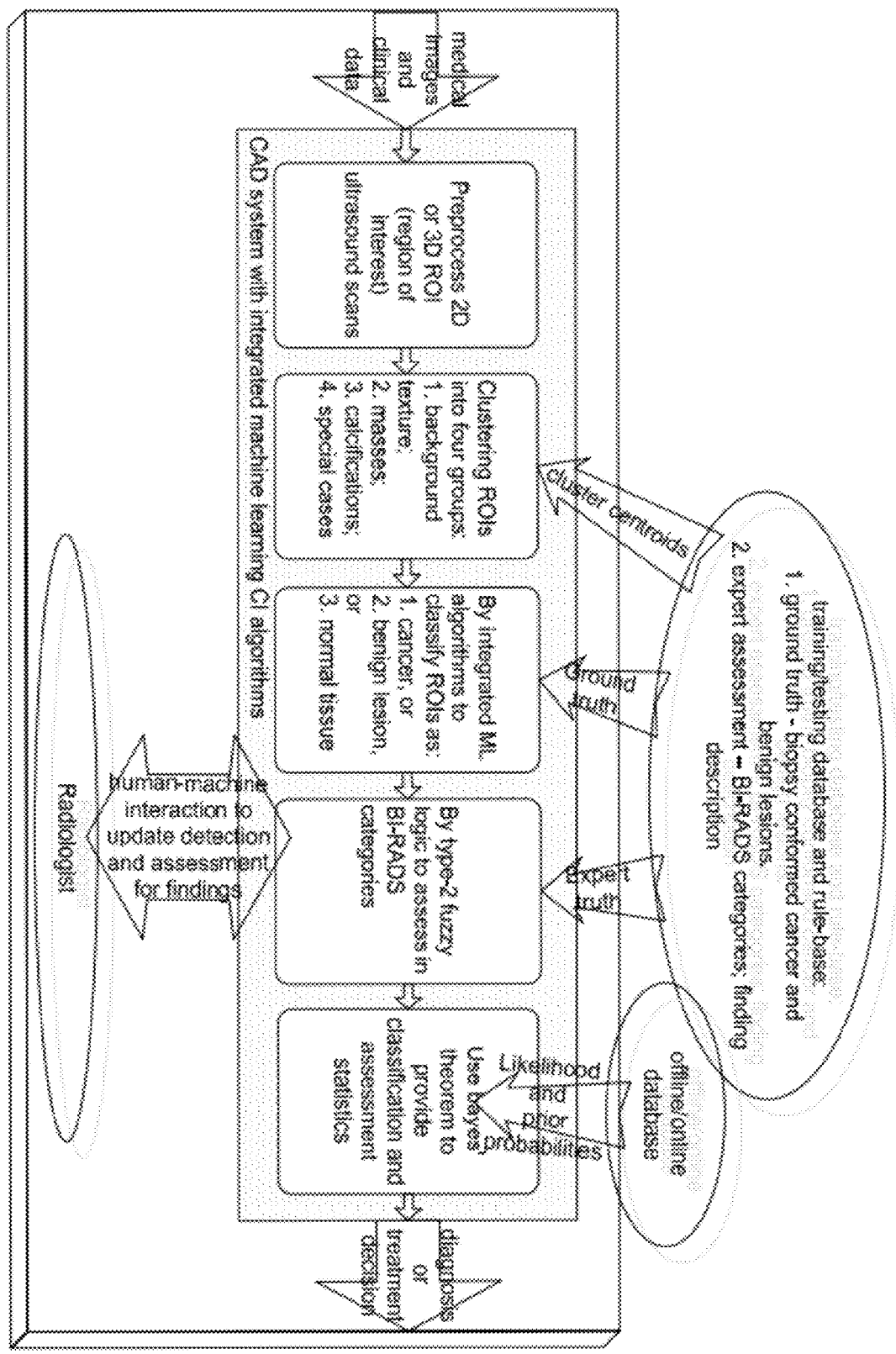

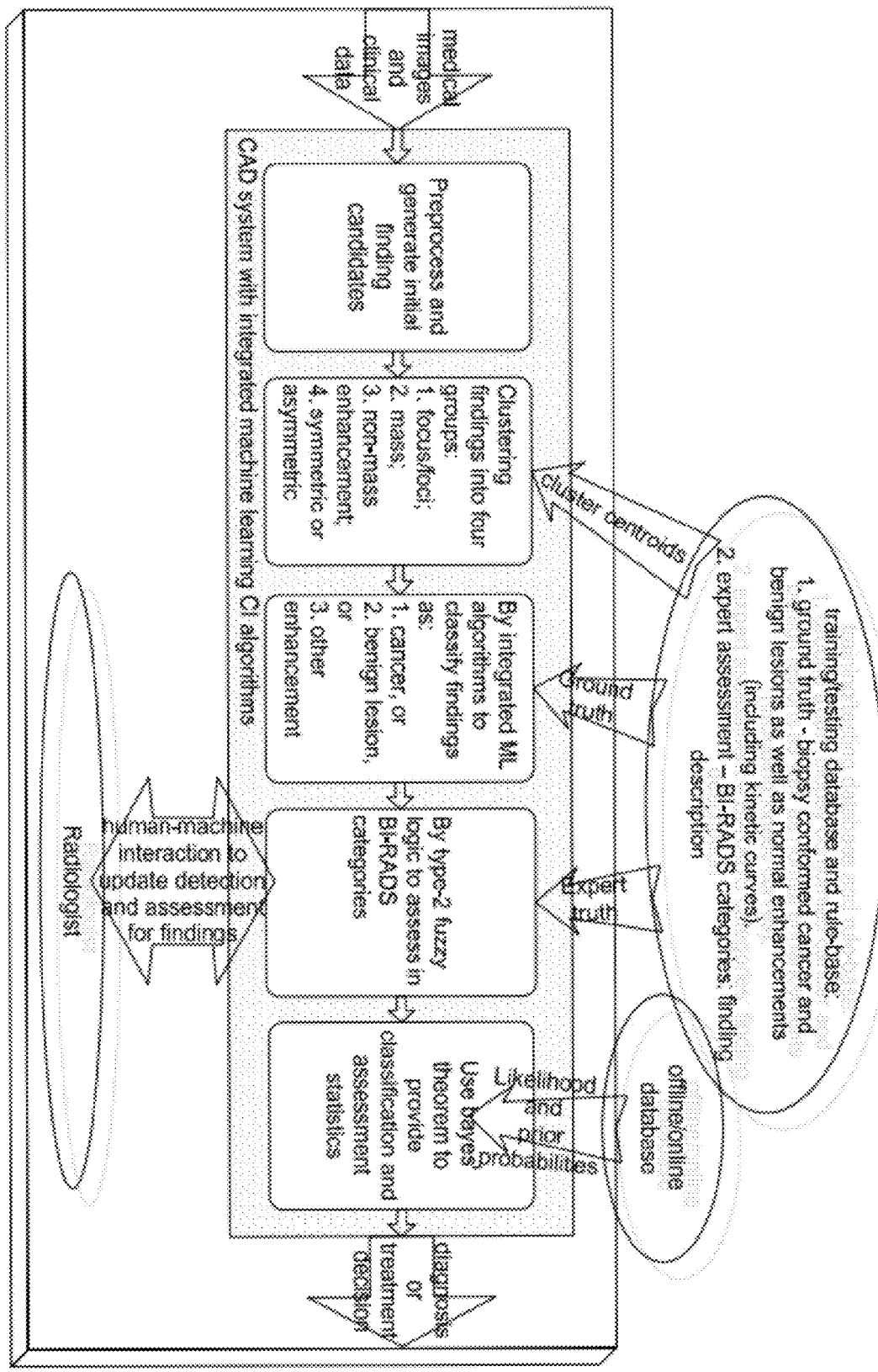

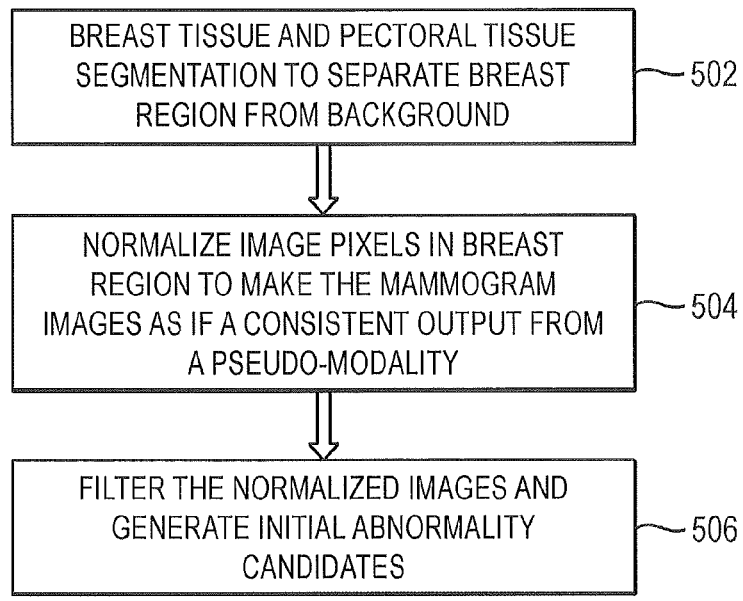
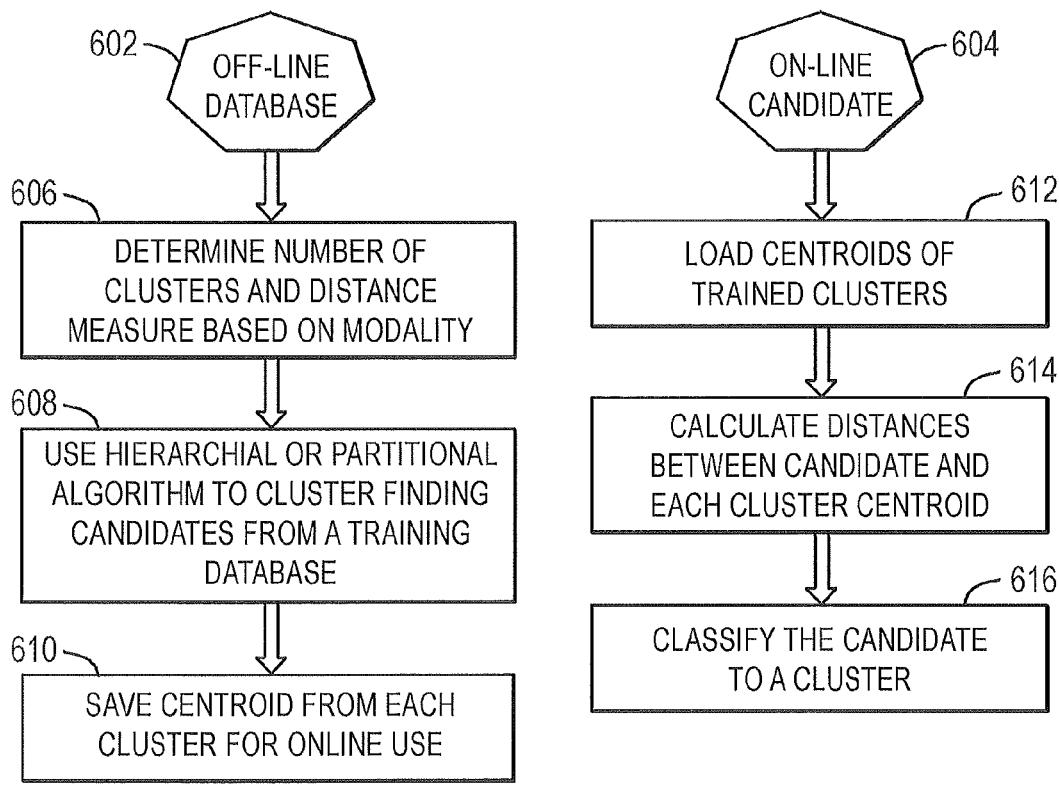

COMBINATION MACHINE LEARNING ALGORITHMS FOR COMPUTER-AIDED DETECTION, REVIEW AND DIAGNOSIS

This application claims priority to U.S. Provisional Application No. 60/919,459, filed on Mar. 23, 2007.

BACKGROUND OF THE INVENTION

Computational intelligence (CI) combines elements of learning, adaptation, evolution and fuzzy logic that are all closely related to machine learning—to allow one to create, in some sense, intelligent applications. CI techniques typically rely on heuristic algorithms in neural networks, fuzzy systems and evolutionary computation. Each of these algorithms has advantages and disadvantages, and many computer-aided, review and diagnosis (abstractly called CAD) applications have used one of these algorithms (see reference list). However, CAD applications for medical imaging systems often require the integration of several of these algorithms to achieve the efficiency and accuracy needed in the radiology practice.

The present invention overcomes the problems associated with the prior art by optimal and integrated use of multiple machine learning algorithms from the computational intelligence methodologies. The technique in the present invention is specifically applied to medical imaging applications in the domain of computer-aided detection and diagnosis of cancer or other abnormality in the human body using expert knowledge, patient clinical information and images from a variety of modalities, such as, digital mammography, ultrasound, MRI or CT.

BRIEF SUMMARY OF THE INVENTION

CI includes neural networks (NN), fuzzy systems (FS) and evolutionary computation (EC).

A neural network is a computing solution that is loosely modeled after cortical structures of the brain. It consists of interconnected processing elements called nodes or neurons that work together to produce an output function. Neural networks are trainable systems that can "learn" to solve complex problems from a set of exemplars and generalize the "acquired knowledge" to solve unforeseen problems as in breast cancer detection from mammograms, i.e., mammography CAD.

A fuzzy system is based on fuzzy logic theory—dealing with reasoning that is approximate rather than precisely deduced from classical predicate logic. There are many applications of fuzzy systems that are in control system. However this invention deals with well thought out real world expert values, such as, language generated by radiologists, for complex diagnosis tasks.

Evolution computation uses non-deterministic methods to adapt behavior over time. Such techniques are inspired by adaptive methods found in nature and solve problems by modeling evolutionary processes. Here we apply those ideas to the interactive progression for a CAD system.

There are three major learning paradigms in CI, each corresponding to a particular abstract learning task: supervised learning, unsupervised learning and reinforcement learning. Most training algorithms can be viewed as a straightforward application of optimization theory and statistical estimation.

This invention utilizes a number of CI techniques with different learning methods in a computer-aided detection, review and diagnosis (CAD) device. Specifically, an unsupervised learning method is used for clustering of types of abnormal findings, such as, lesion types from mammography exams: masses; architectural distortion densities; and calcifications. Then the next step is to classify the findings by type, which could be cancer; benign lesion; or normal tissue. Each classifier is trained with an appropriate learning algorithm, for example, backpropagation algorithm for training a neural network for the relatively simple classifier using a small number of features; and a support vector machine for another classifier using a large number of features. A combined classifier is produced to perform classification task at three different operating points. A fuzzy system is used for assessing the findings in order to generate diagnosis reports in a formal language, such as, BI-RADS categories.

During image review, the device provides some insight as to how it generates its outputs. The output of the device can be updated in an interactive and progressive manor by a human observer (radiologist)—the output from detection or classification of cancer can be updated (or corrected) by the human. Then the updated detection output is fed as inputs to the assessment task. Again the assessment diagnosis output can be updated by a human, and the modified assessment output is fed as input for the machine to produce statistical information. The radiologist uses the statistical information in the final diagnosis report. If so configured, the updated information can be added to an online database so that the device can adapt its behavior based on this new information.

Consistent with some embodiments, there is provided a method of reviewing medical images and clinical data to generate a diagnosis or treatment decision. The method includes receiving, at a computer-aided detection (CAD) system, the medical images and clinical data, processing the medical images and clinical data; to generate initial finding candidates and clustering the initial finding candidates into a plurality of groups. The method further includes classifying, by the CAD system, the initial finding candidates using machine learning algorithms integrated into the CAD system into one or more categories one or more categories of the initial finding candidates using type 2 fuzzy logic, and determining, by the CAD system, detection and assessment statistics based on at least the assessed categories and classified findings using Bayesian probability analysis. The method also includes modifying, by the CAD system, the classified findings and assessed categories based on additional interactive input, and generating the diagnosis or treatment decision based on the determined detection, assessment statistics, and the additional interactive input.

BRIEF DESCRIPTION OF THE SEVERAL VIEWS OF THE DRAWING

FIG. 1 is a flowchart showing a high-level framework for a computer-aided detection method, consistent with some embodiments.

FIG. 2 is a flowchart showing a computer-aided detection method applied to a mammogram, consistent with some embodiments.

FIG. 3 is a flowchart showing a computer-aided detection method applied to an ultrasound, consistent with some embodiments.

FIG. 4 is a flowchart showing a computer-aided detection method applied to a magnetic resonance imaging (MRI) image, consistent with some embodiments.

FIG. 5 is a flowchart showing a method for preprocessing and generating initial finding candidates, consistent with some embodiments.

FIG. 6 is a flowchart showing a method for clustering findings into groups, consistent with some embodiments.

Figure 7:
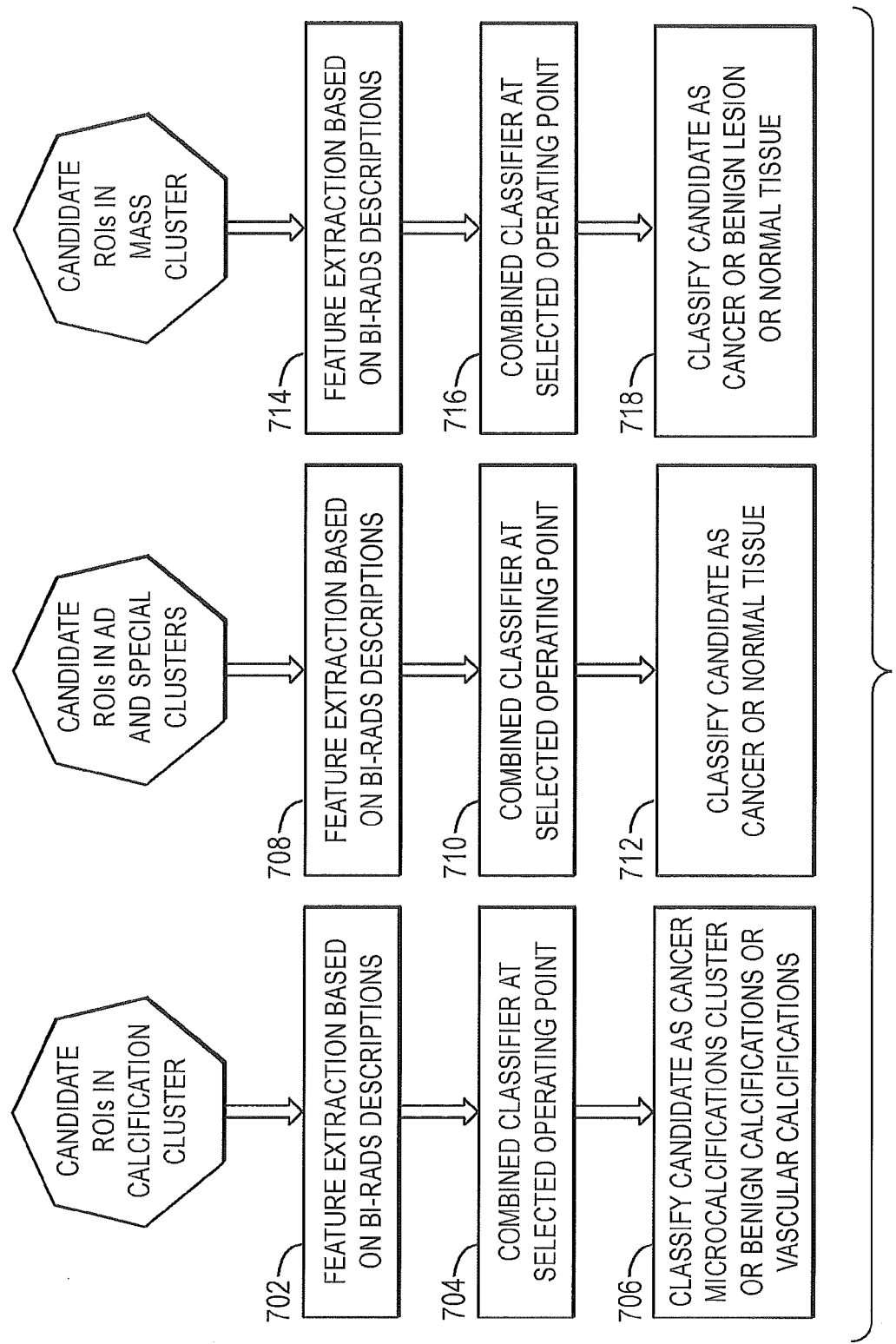
FIG. 7 is a flowchart showing a method for classifying findings, consistent with some embodiments.

In the drawings, elements having the same designation have the same or similar functions.

DETAILED DESCRIPTION OF THE INVENTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

This invention utilizes a number of Computational Intelligence (CI) techniques with different learning methods in a computer-aided detection, review and diagnosis (CAD) device.

FIG. 1 is a flowchart showing a high-level framework for a computer-aided detection system and method, consistent with some embodiments. As shown in FIG. 1, system 100 includes a computer-aided detection (CAD) system having integrated machine learning algorithms 102 coupled to a training/testing database and rule-base 104, and offline or online database 106 and a human reader who may be a radiologist 108. Consistent with some embodiments, medical images and clinical data 110 may be input into CAD system 102 to generate a diagnosis or treatment decision 112. Moreover, CAD system 102 performs a method 114 to generate the diagnosis or treatment decision. Initially, an unsupervised learning method for finding regions of interest (ROI) from training and testing database and rule-base 104 is used to produce a clustering of types of abnormal findings based on the input medical images and clinical data 110 (116). Then, a number of classifiers for each type of findings are trained with appropriate learning algorithms, the training being supervised and using ground truth from testing database and rule-base 104 (118). Consistent with some embodiments, the classifiers are combined in three different manners to produce one classifier that can be operated at three different operating points to find classifications of the abnormal findings. A fuzzy system using expert truth and supervised learning from testing database and rule-base 106 is used for mapping and assessing the findings to diagnostic reports constructed using a formal language (120). Consistent with some embodiments, the findings may be mapped according to the Breast Imaging-Reporting and Data System (BI-RADS). Statistics about the finding is calculated based on Bayesian probability using statistic examination including likelihood and prior probabilities input from offline or online database 106 (122). Finally, diagnosis and treatment decisions are output by CAD system 102 (124). Also in FIG. 1, during image reading, the device provides the readers, such as radiologist 108 some insight as to how it derives its outputs. The output of the device can be updated in an interactive and progressive manner by a human reader (radiologist) 108. The output from classification can be updated by the human 108, and is fed as input to the assessment task (step 120). Again the output from assessment can be updated by the human reader 118, and is fed as input for the machine to produce statistical information (step 122). If so configured, the interactive information can be added to online database 106 so that the device 102 can adapt its future behavior based on the new information.

FIG. 2 is a flowchart showing a computer-aided detection method using system 100 applied to a mammogram, consistent with some embodiments. As shown in FIG. 2, medical images 200 and clinical data are input into CAD system 102 and are initially preprocessed to generate initial finding candidates (202). The initial finding candidates are then clustered into four groups using cluster centroids information from training/testing database and rule-base 104 (204). Consistent with some embodiments, the four groups may include masses, architectural distortion, calcifications, and special cases. The findings are then classified using integrated machine learning algorithms and ground truth from training/testing database and rule-base 104 (206). Consistent with some embodiments, the findings may be classified as cancer, a benign lesion, or normal tissue. Moreover, the ground truth used in the classification may include biopsy conformed cancer and benign lesions as well as the year's follow-up of normal mammograms. Next, type-2 fuzzy logic is applied using expert truth from training/testing database and rule-base 104 to assess the findings according to BI-RADS categories (208). Consistent with some embodiments, the BI-RADS categories may include need additional imaging, negative, benign findings, probably benign findings, suspicious abnormality, highly suspicious malignancy, or proven malignancy. Moreover, the expert truth may include breast density, BI-RADS categories, and finding descriptions. Next, Bayes' theorem is applied using likelihood and prior probabilities from offline or online database 106 to provide detection and assessment statistics (210). Finally, diagnosis and treatment decisions are output by CAD system 102 (212). Throughout, radiologist or other reader 108 may interact with CAD system 102 to update detection and assessment for findings.

FIG. 3 is a flowchart showing a computer-aided detection method using system 100 applied to a breast ultrasound, consistent with some embodiments. As shown in FIG. 3, medical images 300 and clinical data are input into CAD system 102 and are initially preprocessed to generate regions of interest (ROIs) (302). Consistent with some embodiments, the ROIs may be two dimensional (2D) or three dimensional (3D) and from an ultrasound scan. The ROIs are then clustered into four groups using cluster centroids information from training/testing database and rule-base 104 (304). Consistent with some embodiments, the four groups may include background texture, masses, calcifications, and special cases. The findings are then classified using integrated machine learning algorithms and ground truth from training/testing database and rule-base 104 (306). Consistent with some embodiments, the findings may be classified as cancer, a benign lesion, or other enhancement. Moreover, the ground truth used in the classification may include biopsy conformed cancer and benign lesions. Next, type-2 fuzzy logic is applied using expert truth from training/testing database and rule-base 104 to assess the findings according to BI-RADS categories (308). Consistent with some embodiments, the BI-RADS categories may include need additional imaging, negative, benign findings, probably benign findings, suspicious abnormality, highly suspicious malignancy, or proven malignancy. Moreover, the expert truth may include breast density, BI-RADS categories, and finding descriptions. Next, Bayes theorem is applied using likelihood and prior probabilities from offline or online database 106 to provide detection and assessment statistics (310). Finally, diagnosis and treatment decisions are output by CAD system (312). Throughout, radiologist or other reader 108 may interact with CAD system 102 to update detection and assessment for findings.

FIG. 4 is a flowchart showing a computer-aided detection method using system 100 applied to a magnetic resonance imaging (MRI) image of the breast, consistent with some embodiments. As shown in FIG. 4, medical images 400 and clinical data are input into CAD system 102 and are initially preprocessed to generate initial finding candidates (402). The initial finding candidates are then clustered into four groups using cluster centroids information from training/testing database and rule-base 104 (404). Consistent with some embodiments, the four groups may include the four groups may include focus or foci, mass, non-mass enhancement, and symmetric or asymmetric. The findings are then classified using integrated machine learning algorithms and ground truth from training/testing database and rule-base 104 (406). Consistent with some embodiments, the findings may be classified as cancer, a benign lesion, or normal tissue. Moreover, the ground truth used in the classification may include biopsy conformed cancer and benign lesions as well as as well as normal enhancements including kinetic curves. Next, type-2 fuzzy logic is applied using expert truth from training/testing database and rule-base 104 to assess the findings according to BI-RADS categories (408). Consistent with some embodiments, the BI-RADS categories may include need additional imaging, negative, benign findings, probably benign findings, suspicious abnormality, highly suspicious malignancy, or proven malignancy. Moreover, the expert truth may include breast density, BI-RADS categories, and finding descriptions. Next, Bayes theorem is applied using likelihood and prior probabilities from offline or online database 106 to provide detection and assessment statistics (410). Finally, diagnosis and treatment decisions are output by CAD system (412). Throughout, radiologist or other reader 108 may interact with CAD system 102 to update detection and assessment for findings.

The inputs to the above mentioned systems and methods are initial abnormality candidates, generated in steps 202, 302, and 402. FIG. 5 provides a flowchart to produce the initial abnormality candidates, consistent with some embodiments. As shown in FIG. 5, preprocessing includes segmenting breast tissue and pectoral tissue to separate breast region from the background (502). Image pixels in the breast region are then normalized to make the mammogram images as if a consistent output from a pseudo-modality (504). Then, the normalized images are filtered to generate the initial abnormality candidates (506).

Clustering is the partitioning of a data set into subset (clusters), so that the data in each subset share some common trait according to some defined distance measure. Machine learning typically regards data clustering as a form of unsupervised learning. To cluster the initial candidates or ROIs into each lesion types, such as, masses, calcifications. FIG. 6 provides two algorithms: hierarchical algorithm (to find successive clusters using previously established clusters) and partitional algorithm (to determine all clusters at once). The distance measure is selected to determine similarity regarding to typical lesion properties, such as, edge, spicular and pixel normal (distribution) profile. Consistent with some embodiments, the algorithms shown in FIG. 6 may be used in steps 116, 204, 304, and 404, discussed above. As shown in FIG. 6, the two algorithms are performed on an off-line database 602 and with respect to an on-line candidate 604. First, a number of clusters is determined and a distance between the clusters is measured based on modality (606). Finding candidates are clustered using a hierarchical or partitional algorithm from a training database, such as training database 104 (608). The centroid from each cluster is then saved for online use (610). Consistent with some embodiments, the saved centroids may be provided from training database in steps 204, 304, and 404, discussed above. Next, for an on-line candidate, centroids of trained clusters are loaded (612). The distances between the candidate and each cluster centroid are the calculated (614) and the candidate can then be classified to a cluster (616).

FIG. 7 applies the clustering method to mammography CAD to cluster three clusters: calcifications; architecture distortion; and mass density. Consistent with some embodiments, the method shown in FIG. 7 may be used in steps 118, 206, 306, and 406, discussed above. As shown in FIG. 7, for calcification clusters feature extraction is performed based on BI-RADS descriptions (702). A combined classifier is used at a selected operating point (704). Then, the candidate is classified as cancer microcalcifications, benign calcifications, or vascular calcifications (706). For special clusters, feature extraction is performed based on BI-RADS descriptions (708). A combined classifier is used at a selected operating point (710). Then, the candidate is classified as cancer or normal tissue (712). For mass clusters, feature extraction is performed based on BI-RADS descriptions (714). A combined classifier is used at a selected operating point (716). Then, the candidate is classified as cancer or normal tissue (718).

Figure 8:
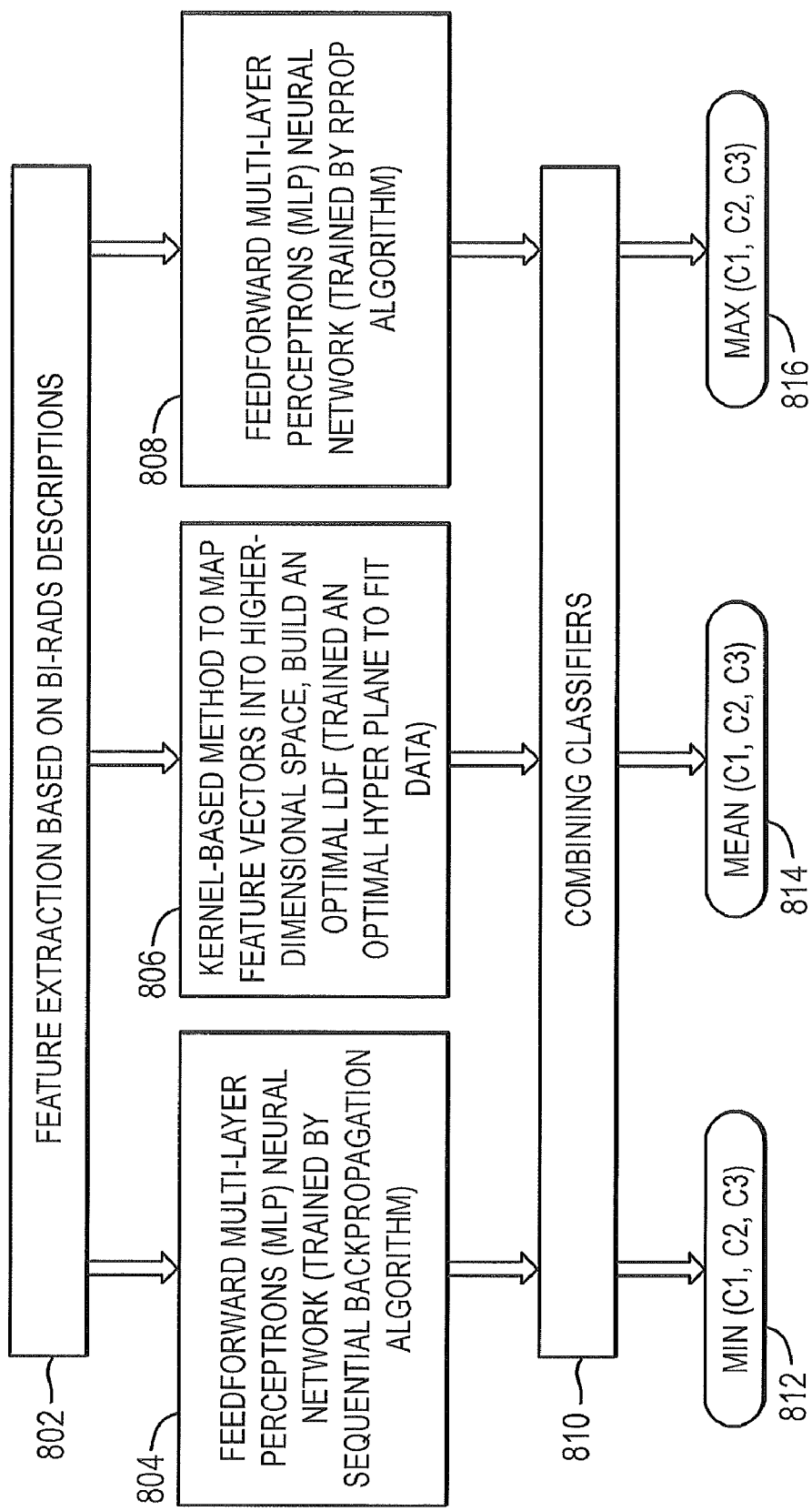
FIG. 8 is a flowchart showing a method for classifying findings using combined classifiers, consistent with some embodiments.

The evolutions of machine learning and pattern analysis algorithms have undergone three revolutions. In the 1960s, it was started from the efficient algorithms for detecting linear relations within data sets. Then in the mid 1980s, to detect the nonlinear relations was posed with the introduction of back-propagation multilayer neural networks and decision tree learning algorithms. Those approaches have been widely applied for classification in CAD (Computer-aided detection) medical applications and commercial products. However these nonlinear algorithms were based on gradient descent so suffered from local minima. Since their statistical behavior was not well understood, they also frequently suffered from overfitting. A more recent approach to pattern recognition known as SVM (State vector machine—one of kernel-based learning methods) enables to analysis nonlinear relations with the efficiency that had previously been reserved for linear algorithms. Furthermore advances in their statistical analysis made it possible to do so in high-dimensional feature spaces while avoiding the dangers of overfitting. However, the kernel-based learning algorithms are usually difficult to adjust a large number of parameters that can be optimally applied to a specific application, especially, to the complex medical imaging detection, review and diagnosis tasks. In this invention, different learning method is used for different lesion type based on complexity of the lesion and number of features extracted for that lesion type. Calcifications can usually be easily characterized as sharp edge of bright spots. So the backpropagation multilayer neural network is used as its classifier. However, architecture distortion (AD) or other special type of lesions are more complicated, and usually requires a large number of features to perform the classification task. The support vector machine (SVM) or other kernel-based methods are used for the AD classifier. The SVM maps feature vectors into higher-dimensional space using some kernel function, and then it builds an optimal linear discriminating function in this space (or an optimal hyperplane that fits into the training data). FIG. 8 then combines different classifiers to produce one classifier, but can operate at three different operating points.

Indeed, FIG. 8 is a flowchart showing a method for classifying findings using combined classifiers, consistent with some embodiments. As shown in FIG. 8, feature extraction is initially performed based on BI-RADS descriptions (802). Then, the extracted features are classified according to three classifiers. The classifiers include feedforward multi-layer perceptrons (MLP) neural network trained by sequential backpropagation algorithm (804), kernel-based method to map feature vectors into higher-dimensional space, build an optimal LDF trained an optimal hyper plane to fit data (806), and feedforward MLP neural network trained by RPROP algorithm (808). Next, the classifiers are combined (810) and a minimum (812), mean or average (814), and maximum (816) are calculated.

Figure 9:
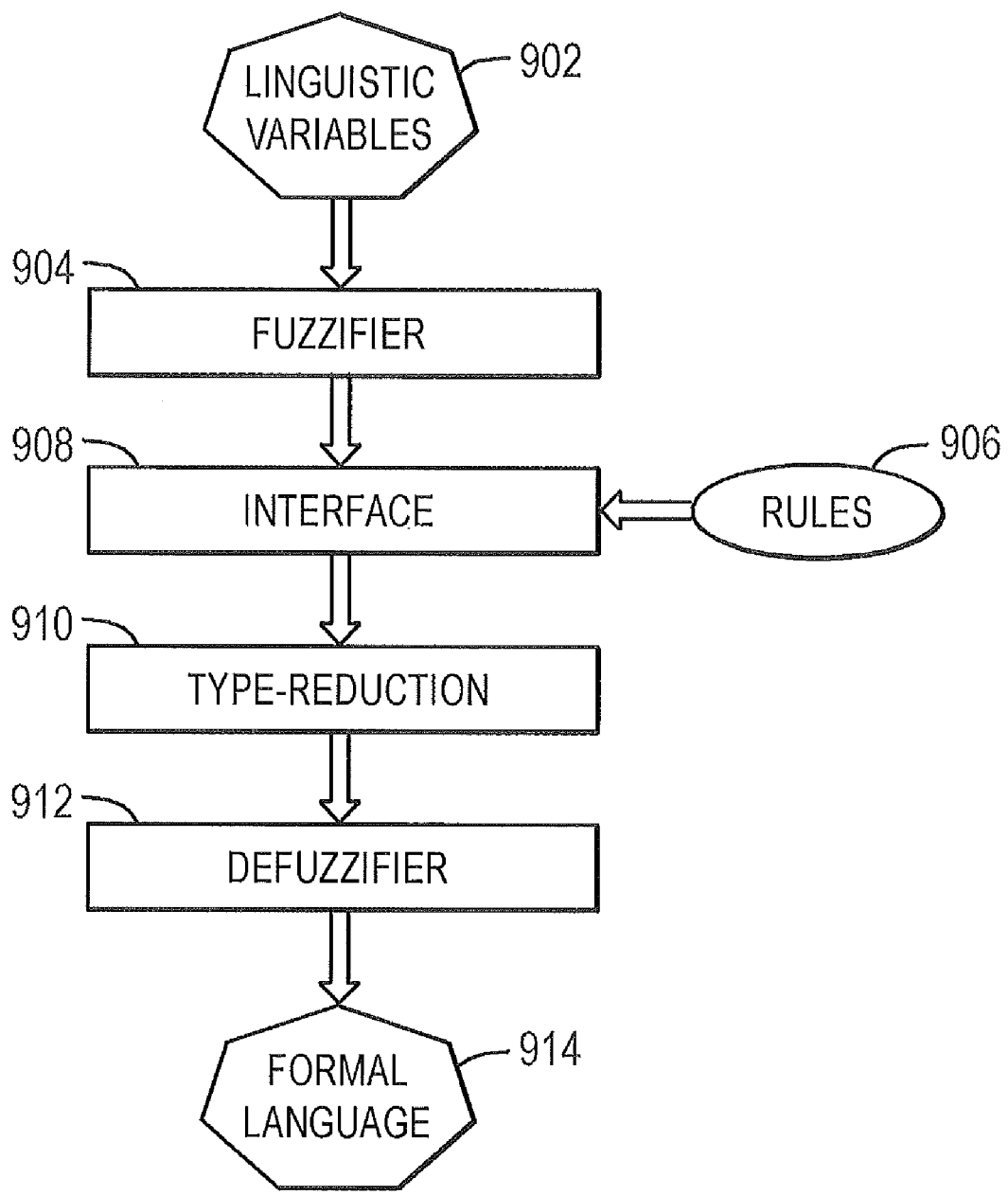
FIG. 9 is a flowchart showing a method for applying type-2 fuzzy logic to assess classified findings based on BI-RADS categories, consistent with some embodiments.

Fuzzy logic deals with reasoning that is approximate rather than precisely deduced from classical predicate logic. The use of fuzzy sets in real computer systems, although rarely in medical imaging device, is extensive in consumer products and control applications. FIG. 9 deals with well thought out real world expert values, such as, radiologists in their linguistic form, for complex diagnosis tasks. The type-2 fuzzy logic takes us one more step toward the goal of "Computing with Words", which lead us to apply this technique to the use of computers to represent human perception, such as, in radiologists' decision making process for cancer detection and assessment in mammography. Type-2 fuzzy logic offers an opportunity to model levels of uncertainty with which traditional fuzzy logic (type-1) struggles. The perceptions (for example, perceptions of breast density or BI-RADS category, or even optimal image contrast) cannot be modeled by traditional mathematical techniques and that fuzzy logic is more suitable. Since they have non-crisp fuzzy membership functions, the type-2 fuzzy logic can model these perceptions more effectively than type-1 fuzzy sets whose membership grades are crisp in nature. A fuzzy rule-based system is used with NN techniques for training and/or adaptation.

FIG. 9 is a flowchart showing a method for applying type-2 fuzzy logic to assess classified findings based on BI-RADS categories, consistent with some embodiments. Consistent with some embodiments, the algorithms shown in FIG. 6 may be used in steps 120, 208, 308, and 408, discussed above. Linguistic variables (902) are input into a fuzzifier (904). Rules (906) are put into an interface (908) along with the output from the fuzzifier. Then type-reduction is performed on the results (910). A defuzzifier is applied to the reduced results (912), and the defuzzified results are translated into formal language (914).

Bayesian decision theory is a fundamental statistical approach to the problem of pattern classification. This approach is based on quantifying the tradeoffs between various classification decision using probability and the costs that accompany such decision. It makes the assumption that the decision problem is posed in probabilistic terms, and that all of the relevant probability values are known.

$$P(\omega_j|x)=p(x|\omega_j)P(\omega_j)/p(x) \quad \text{Bayes Formula}$$

where $$p(x)=\Sigma_j p(x|\omega_j)P(\omega_j)$$

Bayes formula shows that by observing the feature vector x we can convert the prior probability $P(\omega_j)$ to the posteriori probability $P(\omega_j|x)$—the probability of the state of nature being $\omega_j$ given the feature vector values x.

The $p(x|\omega_j)$ is the likelihood of $\omega_j$ with respect to x. For example, if the state $\omega_j$ is being cancer, $p(x|\omega_j)$ is the cancer probability density function of the feature vector x. The other states of $\omega$ can be benign lesion, or normal tissue.

Figure 10:
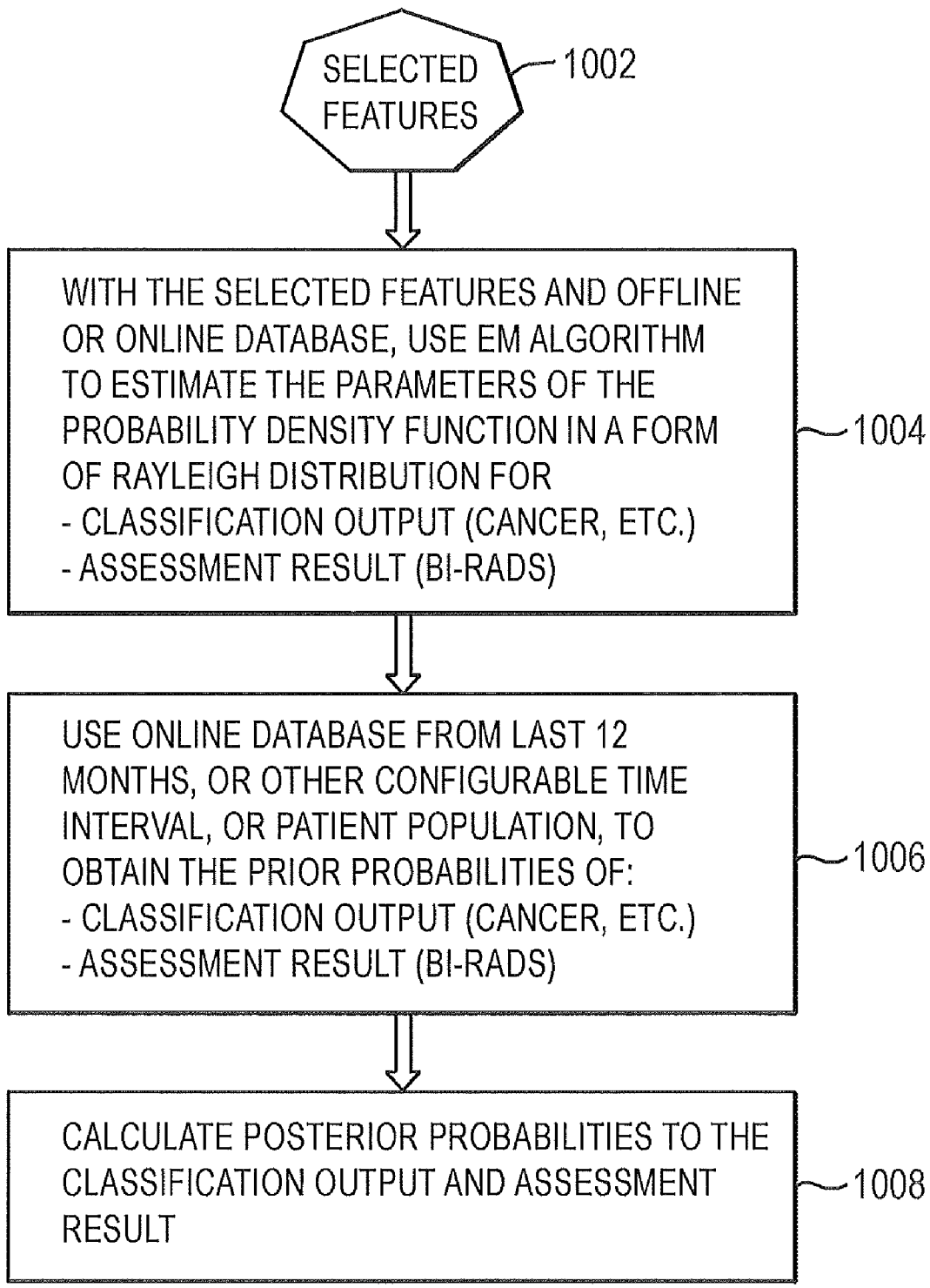
FIG. 10 is a flowchart showing a method for applying Bayesian probability analysis to classification and assessment results, consistent with some embodiments.

The probability density function is modeled by Gaussian distribution in many other medical applications. However, the cancer detection system, the probability density functions show a particular skewed distribution, and more likely to be Rayleigh distribution. FIG. 10 is a flowchart showing a method for applying Bayesian probability analysis to classification and assessment results, consistent with some embodiments. Consistent with some embodiments, the algorithms shown in FIG. 10 may be used in steps 122, 210, 310, and 410, discussed above. In FIG. 10, the Expectation-Maximization (EM) algorithm is used to estimate the parameters of the probability density function in a form of Rayleigh mixture distribution. The EM algorithm is used on selected features (1002) and likelihood and past probabilities from offline or online database 106 to estimate the parameters of the probability density function in a form of Rayleigh distribution for classification output and BI-RADS assessment results (1004). The prior probabilities of the classification output and BI-RADS assessment results over last 12 months or other configurable time interval, or patient population, are obtained from offline or online database 106 (1006). From these inputs, posteriori probabilities to the classification output and BI-RADS assessment results are calculated (1008).

Consistent with embodiments described herein, a system and method are provided for reviewing medical images and clinical data using machine learning algorithms, fuzzy logic, Bayesian probabilities, and interactive human input to generate a diagnosis or treatment decision. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. A method of reviewing medical images and clinical data to generate a diagnosis or treatment decision, comprising:
    receiving, at a computer-aided detection (CAD) system, the medical images and clinical data;
    processing, by the CAD system, the medical images and clinical data; to generate initial finding candidates;
    clustering, by the CAD system, the initial finding candidates into a plurality of groups;
    classifying, by the CAD system, the initial finding candidates into one or more categories using machine learning algorithms integrated into the CAD system and combined classifiers;
    assessing, by the CAD system, one or more categories of the initial finding candidates using type 2 fuzzy logic;
    determining, by the CAD system, detection and assessment statistics based on at least the assessed categories and classified findings using Bayesian probability analysis;
    modifying, by the CAD system, the classified findings and assessed categories based on additional interactive input; and
    generating the diagnosis or treatment decision based on the determined detection, assessment statistics, and the additional interactive input.

2. The method of claim 1, wherein processing the medical images and clinical data comprises:
    segmenting a region of interest from a background;
    normalizing the region of interest;
    filtering the normalized region of interest; and generating the initial finding candidates from the normalized region of interest.

3. The method of claim 1, wherein clustering the initial finding candidates into a plurality of groups comprises:
   determining a number of clusters stored in a database;
   measuring a distance between the clusters based on modality;
   clustering the initial finding candidates using a hierarchical or partitional algorithm; and
   saving a centroid from each initial finding candidate cluster.

4. The method of claim 3, wherein clustering the initial finding candidates into a plurality of groups further comprises:
   loading saved centroids;
   calculating distances between at least one candidate of the initial finding candidates and each loaded centroid; and
   classifying the at least one candidate of the initial finding candidates based on the calculated distance.

5. The method of claim 1, wherein classifying the initial finding candidates comprises:
   extracting selected features from the initial finding candidates;
   performing, by the CAD system, a first classification using a first neural network trained by a first algorithm;
   performing, by the CAD system, a second classification using a kernel-based method to map feature vectors of the extracted features into higher-dimensional space;
   performing, by the CAD system, a third classification using a second neural network trained by a second algorithm;
   combining the first, second, and third classifications; and
   determining, by the CAD system, a minimum for each classification, a mean for each classification, and a maximum for each classification.

6. The method of claim 1, wherein assessing one or more categories of the initial finding candidates using type 2 fuzzy logic comprises:
   inputting linguistic variables into a fuzzifier to generate fuzzified results;
   inputting the fuzzified results and additional rules into an interface;
   reducing the fuzzified results by type;
   defuzzifying the reduced results; and
   translating the defuzzified results into formal language.

7. The method of claim 1, wherein determining detection and assessment statistics based on at least the assessed categories and classified findings using Bayesian probability analysis comprises:
   estimating parameters of a probability density function in a form of Rayleigh distribution using an expectation-maximization algorithm;
   obtain prior probabilities; and
   calculate posteriori probabilities of the assessed categories and classified results using the estimated parameters and prior probabilities.

8. The method of claim 1, wherein the additional interactive input is provided by a human observer.

* * * * *